US00PP21602P2

(12) United States Plant Patent

Clark et al.

(10) Patent No.: US PP21,602 P2

(45) Date of Patent: Dec. 28, 2010

(54) *COLEUS* PLANT NAMED 'UF06419'

(50) Latin Name: *Solenostemon scutellarioides*
Varietal Denomination: UF06419

(75) Inventors: David G. Clark, Gainesville, FL (US); Phuong N. Nguyen, Oceano, CA (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/590,655

(22) Filed: Nov. 12, 2009

(51) Int. Cl.
*A01H 5/00* (2006.01)

(52) U.S. Cl. ..... Plt./373

(58) Field of Classification Search ..... Plt./373, Plt./263.1

See application file for complete search history.

*Primary Examiner*—Kent L Bell

(74) *Attorney, Agent, or Firm*—Jondle & Associates, P.C.

(57) ABSTRACT

'UF06419' is a new *coleus* plant distinguished by foliage having bright red-orange centers with a yellow border along the leaf margins. It has a vigorous growth and branching habit, and good sun and heat tolerance. It has desirable characteristics that allow it to retain its leaves in the garden landscape for an extended period of time during the normal growth season compared to most *coleus* varieties. It is an excellent variety for commercial production due to excellent adventitious rooting characteristics of vegetative propagules (cuttings), and subsequent vigorous growth in greenhouse conditions. 'UF06419' has proven to be an excellent performing variety in preliminary outdoor trials across the United States, and should be an excellent choice to add vibrant long lasting annual color to gardens across the United States, Canada, and Europe.

2 Drawing Sheets

Genus and species: *Solenostemon scutellarioides.*

Variety denomination: 'UF06419'.

BACKGROUND OF THE INVENTION

The invention relates to a new and distinct variety of *coleus* plant named 'UF06419'. 'UF06419' originated from an open pollination conducted in March 2006 in Gainesville, Fla. between the female *coleus* plant 'Elfers' (unpatented) and an unknown male *coleus* plant. A single seedling was chosen in March 2006 for further asexual propagation in Gainesville, Fla.

'UF06419' has been reproduced asexually for over three and one-half years through vegetative cuttings and has been found to retain its distinctive characteristics through successive asexual propagations via vegetative cuttings.

Plant Breeder's Rights for this variety have been applied for in Canada on Mar. 13, 2009. 'UF06419' has not been made publicly available more than one year prior to the filing date of this application.

SUMMARY OF THE INVENTION

The following are the most outstanding and distinguishing characteristics of 'UF06419' when grown under normal horticultural practices in Gainesville, Fla.

1. Foliage having mainly bright red-orange color with a bright yellow border along the leaf margins;
2. A vigorous growth and branching habit;
3. Foliage retention for an extended period of time;
4. Good sun and heat tolerance; and 5. Good performance in a wide variety of garden conditions.

DESCRIPTION OF THE PHOTOGRAPHS

This new *coleus* plant is illustrated by the accompanying photographs which show the plant's form and foliage. The colors shown are as true as can be reasonably obtained by conventional photographic procedures. The photographs were taken from 3-month-old plants grown from cuttings in 1 gallon pots during summer 2009 in Gainesville, Fla.

DESCRIPTION OF THE NEW VARIETY

Figure 1:
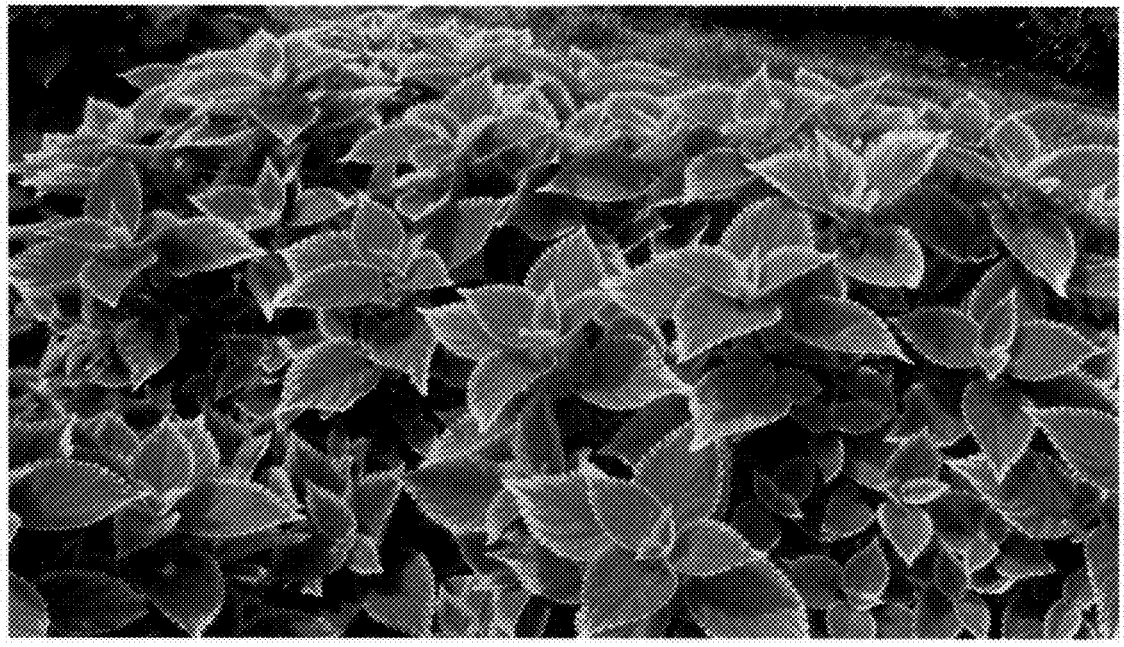
FIG. 1 shows the growth habit, form, and foliage of the instant plant.
Figure 2:
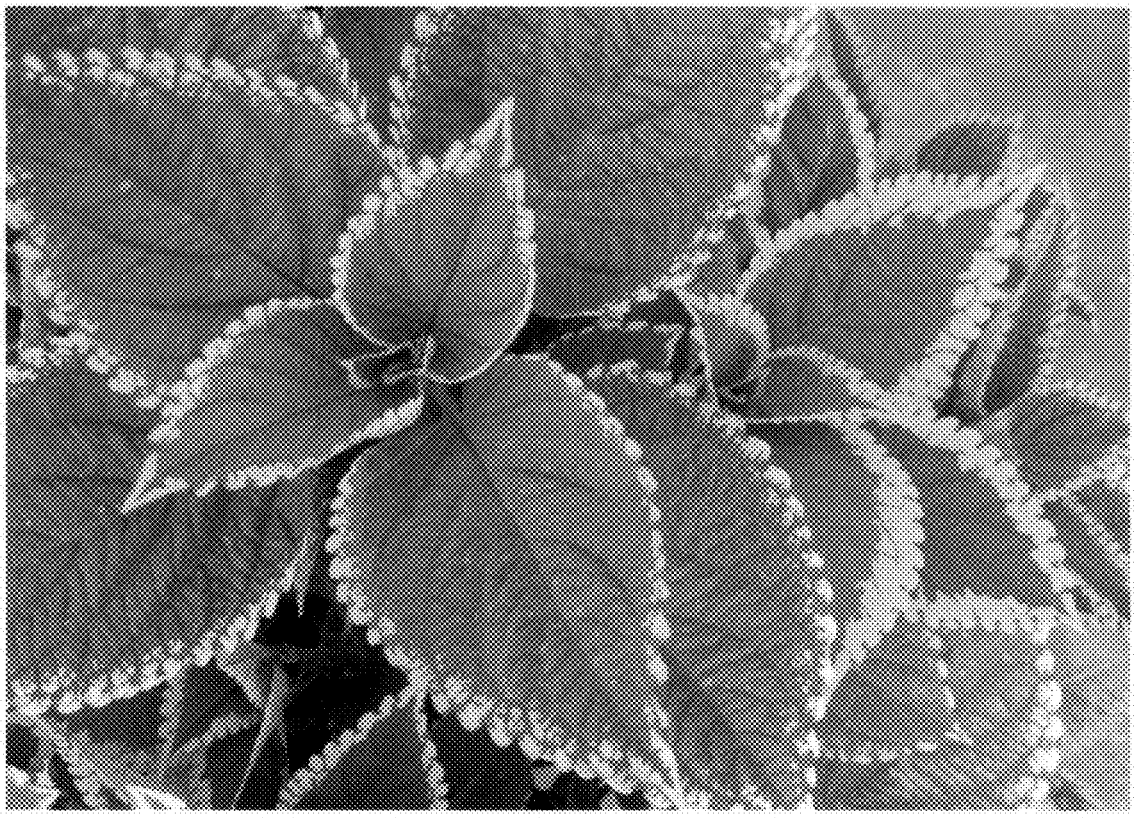
FIG. 2 shows a close-up of the foliage.

The following detailed description sets forth the distinctive characteristics of 'UF06419'. The detailed description was taken on 3-month-old plants from cuttings, growing in a greenhouse in 1 gallon pots in Gainesville, Fla. in summer 2009. The plants were pinched one month after cutting. Color references are to The R.H.S. Colour Chart of The Royal Horticultural Society of London (R.H.S.), 2001 Edition.

DETAILED BOTANICAL DESCRIPTION

Classification:

*Family.*—Lamiaceae.

*Botanical.*—*Solenostemon scutellarioides.*

*Common name.*—*Coleus.*

*Variety name.*—'UF06419'.

Plant description:

*Form.*—Upright.

*Habit.*—Medium-tall with uniform branching.

*Height* (*from top of soil*).—140.0 cm.
*Width* (*horizontal plant diameter*).—90.0 cm.

Propagation:
*Type cuttings.*—Vegetative meristems having at least 2 nodes.
*Time to initiate roots.*—7 days.
*Time to produce a rooted cutting.*—14 days.
*Root habit.*—Freely branching.
*Root description.*—Callus forms in 3 to 5 days, roots initiate in 7 days and become a highly branched cutting in 14 days.

Branches:
*Quantity per plant.*—20 to 22 per plant, pinched once.
*Branch color.*—RHS 154D (Yellow-green) streaked with RHS 51B (Red).
*Texture.*—Smooth.
*Pubescence.*—Absent.
*Stem description.*—Square-shaped stem, 1.5 cm in diameter at the soil line.
*Branch diameter.*—0.6 cm at the base of a 37.0 cm long branch.
*Branch length.*—37.0 cm.
*Internode length.*—7.0 cm.
*Anthocyanin.*—RHS 51B (Red).

Leaves:
*Quantity of leaves per branch.*—14 to 16.
*Arrangement.*—Opposite pairs of leaves per node, nodes arranged perpendicular to each other.
*Fragrance.*—Absent.
*Shape.*—Rounded-acute.
*Length.*—12.0 cm.
*Width.*—7.0 cm.
*Apex.*—Acute.
*Base.*—Rounded.
*Margin.*—Crenate.
*Leaf texture* (*both surfaces*).—Smooth.
*Pubescence* (*both surfaces*).—Absent.
*Venation color, upper surface.*—The center is RHS 51B (Red) with RHS 6D (Yellow) margins.
*Color, mature and immature leaf.*—Upper surface: The center is RHS 51B (Red) with 1.0 cm RHS 6D (Yellow) margins. Lower surface: RHS 6D (Yellow).
*Petiole length.*—3.5 cm to 4.0 cm.
*Petiole diameter.*—0.4 cm.
*Petiole color.*—RHS 154D (Yellow-green) streaked with RHS 51B (Red).

Flowers and seeds: Flowers and seeds have not been observed.

Disease and insect resistance: Disease and insect resistance is typical of the species.

COMPARISON WITH PARENTAL LINES AND KNOWN VARIETY

When 'UF06419' is compared to the female parent 'Elfers' (unpatented), 'UF06419' has uniform red-orange leaves with bright yellow margins, while 'Elfers' has multicolored leaves of maroon, pink, and green, with spots of yellow.

When 'UF06419' is compared to the commercial, variety Versa collection 'Crimson Gold' (patent status unknown), 'UF06419' has larger leaves, more vigor during production, and a more compact branching habit. 'UF06419' also has brighter red-orange color in the center of the leaf than 'Crimson Gold' with similar yellow margins. Additionally, 'UF06419' is produced from vegetative cuttings, and is faster to a saleable plant than 'Crimson Gold', which is propagated from seeds.

We claim:

1. A new and distinct variety of *Coleus* plant as shown and described herein.

* * * * *